US011568536B2

United States Patent
Luengo Hendriks et al.

(10) Patent No.: US 11,568,536 B2
(45) Date of Patent: Jan. 31, 2023

(54) METHOD FOR DIGITALLY GENERATING SCORES FOR MULTIPLE DIAGNOSTIC TESTS FROM TISSUE ASSAYED WITH A SINGLE TEST

(71) Applicant: Flagship Biosciences, Inc., Westminster, CO (US)

(72) Inventors: Cris L Luengo Hendriks, Broomfield, CO (US); Joseph Krueger, Andover, MA (US); Nathan T. Martin, Seattle, WA (US); Joshua C. Black, Aurora, CO (US)

(73) Assignee: Flagship Biosciences, Inc, Westminster, CO (US)

( * ) Notice: Subject to any disclaimer, the term of this patent is extended or adjusted under 35 U.S.C. 154(b) by 463 days.

(21) Appl. No.: 16/862,098

(22) Filed: Apr. 29, 2020

(65) Prior Publication Data
US 2021/0343004 A1    Nov. 4, 2021

(51) Int. Cl.
*G06T 7/00* (2017.01)
*G16H 50/30* (2018.01)
(Continued)

(52) U.S. Cl.
CPC ........ *G06T 7/0012* (2013.01); *G01N 33/4833* (2013.01); *G01N 33/53* (2013.01); *G06N 20/00* (2019.01); *G16H 50/30* (2018.01); *G06T 2207/20081* (2013.01); *G06T 2207/30024* (2013.01)

(58) Field of Classification Search
CPC ......... G06T 7/0012; G06T 2207/20081; G06T 2207/30024; G01N 33/4833; G01N 33/53; G06N 20/00; G16H 20/10; G16H 50/30; G16H 50/70
See application file for complete search history.

(56) References Cited

U.S. PATENT DOCUMENTS

| 2010/0184093 A1* | 7/2010 | Donovan | G16H 50/50 |
| | | | 435/287.1 |
| 2016/0110584 A1* | 4/2016 | Remiszewski | G06V 20/69 |
| | | | 382/133 |
| 2018/0089495 A1* | 3/2018 | Black | G06V 10/42 |

OTHER PUBLICATIONS

Luo et al., "A Quantitative Assessment of Factors Affecting the Technological Development and Adoption of Companion Diagnostics", Frontiers in genetics vol. 6 357. Jan. 28, 2016, pp. 1-12 (Year: 2016).*

(Continued)

*Primary Examiner* — Nay A Maung
*Assistant Examiner* — Jose M Torres

(57) ABSTRACT

One type of tissue-based assay, the companion diagnostic ("CDx") allows for the identification of individuals within a larger patient population who are more likely to respond to a therapy. The CDx paradigm typically applies to drugs that target a specific gene product or biologic pathway involving a gene product of interest. It is possible, especially for popular therapeutic targets, for multiple drugs and multiple associated CDx to be developed for a single gene product or biologic pathway involving the gene product. Currently, each of these similar CDx must be applied to identify the best therapy. The present invention can determine the outcome of one CDx using an image of a tissue section used for another CDx. Using a single tissue section and a single CDx, it becomes possible to obtain the outcome of multiple, related CDx.

13 Claims, 4 Drawing Sheets

(51) Int. Cl.
     *G06N 20/00*      (2019.01)
     *G01N 33/483*     (2006.01)
     *G01N 33/53*      (2006.01)

(56) References Cited

OTHER PUBLICATIONS

Olsen et al., "Companion diagnostics for targeted cancer drugs—clinical and regulatory aspects", Frontiers in oncology vol. 4 105. May 16, 2014, pp. 1-8 (Year: 2014).*

* cited by examiner

METHOD FOR DIGITALLY GENERATING SCORES FOR MULTIPLE DIAGNOSTIC TESTS FROM TISSUE ASSAYED WITH A SINGLE TEST

CROSS-REFERENCE TO RELATED APPLICATION

This application is a continuation-in-part and of commonly owned U.S. application Ser. No. 15/396,123, filed 30 Dec. 2016, titled "METHOD FOR DIGITALLY GENERATING SCORES FOR MULTIPLE DIAGNOSTIC TESTS FROM TISSUE ASSAYED WITH A SINGLE TEST"; which claims benefit of priority with U.S. Provisional Application Ser. No. 62/302,273, filed Mar. 2, 2016, titled "METHOD FOR DIGITALLY GENERATING SCORES FOR MULTIPLE DIAGNOSTIC TESTS FROM TISSUE ASSAYED WITH A SINGLE TEST", the content of which are hereby incorporated by reference.

BACKGROUND

Field of the Invention

This application relates generally to methods for image analysis of tissue sections. More specifically, this application relates to extracting information from a digital image of a tissue section assayed with a tissue-based test which predicts patient response to a specific drug targeting a gene product or biological pathway/mechanism involving a gene product.

Description of the Related Art

Tissue-based assays are used to determine diagnosis of disease, disease severity, disease progression, candidacy for a particular therapy, and therapy efficacy of patients. One type of tissue-based assay, the companion diagnostic ("CDx") allows for the identification of individuals within a larger patient population who are more likely to respond to a therapy.

The CDx paradigm typically applies to drugs that target a specific gene product or biologic pathway involving a gene product of interest. The gene product itself, or other gene products in the biologic pathway can be assayed to gain insights into the status of the disease and these assessments can be utilized to guide patient treatment decisions as described above.

Examples of the CDx paradigm are HERCEPTIN® and HER2 protein expression testing by immunohistochemistry or fluorescent in situ hybridization methods and XALKORI® and evaluation of ALK protein expression testing by immunohistochemistry.

It is possible, especially for popular therapeutic targets, for multiple drugs and multiple associated CDx to be developed for a single gene product or biologic pathway involving the gene product. The current CDx and complimentary diagnostic paradigms are one-test-for-one drug, requiring the use of multiple tests for multiple drugs, even if the multiple drugs target identical gene products or biologic pathways, as seen in FIG. 1. Due to the presence of multiple tests and multiple drugs, there is a possibility for the misuse of both the diagnostic tests and prescription of the related drugs within the practical constrains of the clinical environment.

For example, a specific hospital may have the equipment and expertise to perform the CDx for Protein A developed by Diagnostic Manufacturer A for Drug A, and prefers to prescribe Drug B, but is unable to support the CDx developed by Diagnostic Manufacturer B to support Drug B. In this example, the hospital or lab may run the Drug A CDx and use the result of that test to prescribe Drug B, which is not the intended use for which the CDx was validated for or approved for by the relevant regulatory agency. In these instances, there is greater chance for error in guiding patient treatment decisions and utilization of a diagnostic test outside of the conditions for which it was validated and approved.

It is becoming increasingly more common for multiple drugs to be developed which target the same gene product or biologic pathway involving the same gene product. A method for generating a plurality of CDx scores matched to different drugs targeting the same gene product or biologic pathway from a single CDx would be beneficial to facilitate use of these life-saving drugs in the clinic within the technical, expertise, and workflow constraints of clinical implementation of tissue-based diagnostics.

SUMMARY

In accordance with the embodiments herein, methods are described for extracting information from patient tissues assayed with one tissue-based test and transforming said information to generate virtual scores for one or more different, but related CDx. Generally, the method entails the follow four steps: i) obtaining a digital image of a tissue section that has been assayed with a tissue-based test; ii) applying an algorithm process, implemented by a computer, to the digital image to extract the image analysis features of tissue objects within the tissue section; iii) applying a mapping function to the image analysis features to calculate a virtual diagnostic score, where the virtual diagnostic score is one that would have been obtained if the tissue section had been assayed with a different tissue-based test; and iv) determining a patient status for the patient that provided the tissue section.

DETAILED DESCRIPTION OF EMBODIMENTS

In the following description, for purposes of explanation and not limitation, details and descriptions are set forth in order to provide a thorough understanding of the present invention. However, it will be apparent to those skilled in the art that the present invention may be practiced in other embodiments that depart from these details and descriptions without departing from the spirit and scope of the invention.

For purpose of definition, a tissue object is one or more of a cell (e.g., immune cell), cell sub-compartment (e.g., nucleus, cytoplasm, membrane, organelle), cell neighborhood, a tissue compartment (e.g., tumor, tumor microenvironment (TME), stroma, lymphoid follicle, healthy tissue), blood vessel, a lymphatic vessel, vacuole, collagen, regions of necrosis, extra-cellular matrix, a medical device (e.g., stent, implant), a gel, a parasitic body (e.g., virus, bacterium), a nanoparticle, a polymer, and/or a non-dyed object (e.g., metal particle, carbon particle). Tissue objects are visualized by histologic stains which highlight the presence and localization of a tissue object. Tissue objects can be identified directly by stains specifically applied to highlight the presence of said tissue object (e.g., hematoxylin to visualize nuclei, immunohistochemistry stain for a protein specifically found in a muscle fiber membrane), indirectly by stains applied which non-specifically highlight the tissue compartment (e.g., DAB background staining), are biomarkers known to be localized to a specific tissue compartment (e.g., nuclear-expressed protein, carbohydrates only found in the cell membrane), or can be visualized without staining (e.g., carbon residue in lung tissue).

For the purpose of this disclosure, patient status includes diagnosis of inflammatory status, disease state, disease severity, disease progression, therapy efficacy, and changes in patient status over time. Other patient statuses are contemplated.

For the purpose of this disclosure, a therapeutic methodology is one of a medication, a combination of medication, a treatment plan, or a therapy. A "drug" or "Drug", as referred to in this disclosure, means a therapeutic methodology.

In an illustrative embodiment of the invention, the method may generally comprise four consecutive steps, including i) obtaining a digital image of a tissue section that has been assayed with a tissue-based test; ii) applying an algorithm process, implemented by a computer, to the digital image to extract the image analysis features of tissue objects within the tissue section; iii) applying a mapping function to the image analysis features to calculate a virtual diagnostic score, where the virtual diagnostic score is one that would have been obtained if the tissue section had been assayed with a different tissue-based test; and iv) determining a patient status for the patient that provided the tissue section.

Figure 2:
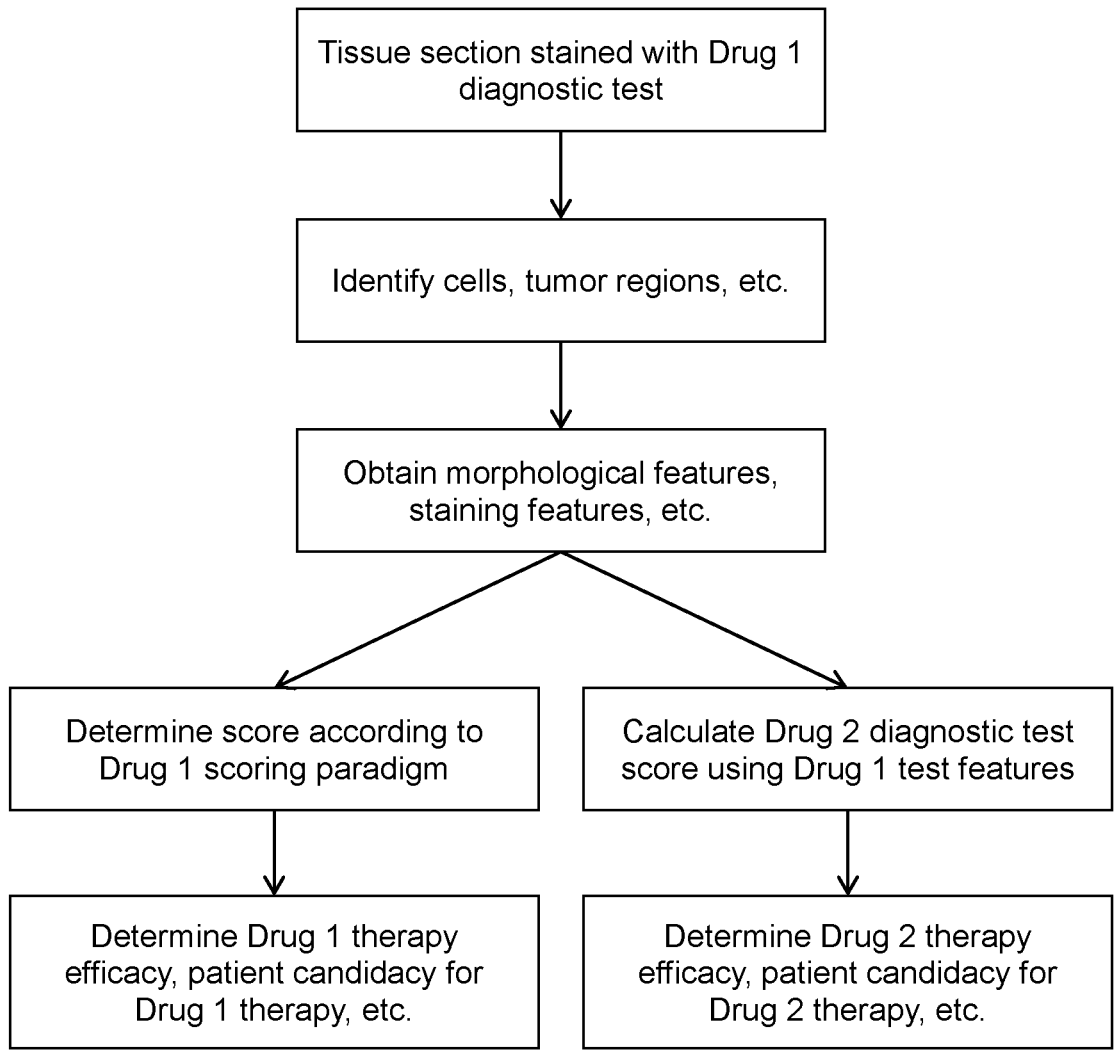
FIG. 2 illustrates a general overview of the method of the present invention.

FIG. 2 outlines an example of the process to arrive at a patient treatment decision for a second drug (Drug 2) based on tissue assayed with a first drug's (Drug 1) CDx. Within the scope of the invention, both Drug 1 and Drug 2 target the same gene product or biologic pathway involving the same gene product. In this embodiment, a tissue section is stained with the test for Drug 1. After the tissue section is stained, tissue objects within the tissue section are identified. These tissue objects have their image analysis features extracted via a computer algorithm process. These image analysis features would typically be used to determine a score for the tissue section for the test for Drug 1. In the present invention, the image analysis features are mapped to what they would be if the test for Drug 2 had been applied to the tissue section. This allows for a clinician to determine if Drug 2 is a good choice for the patient from whom the tissue section is taken.

Figure 1:
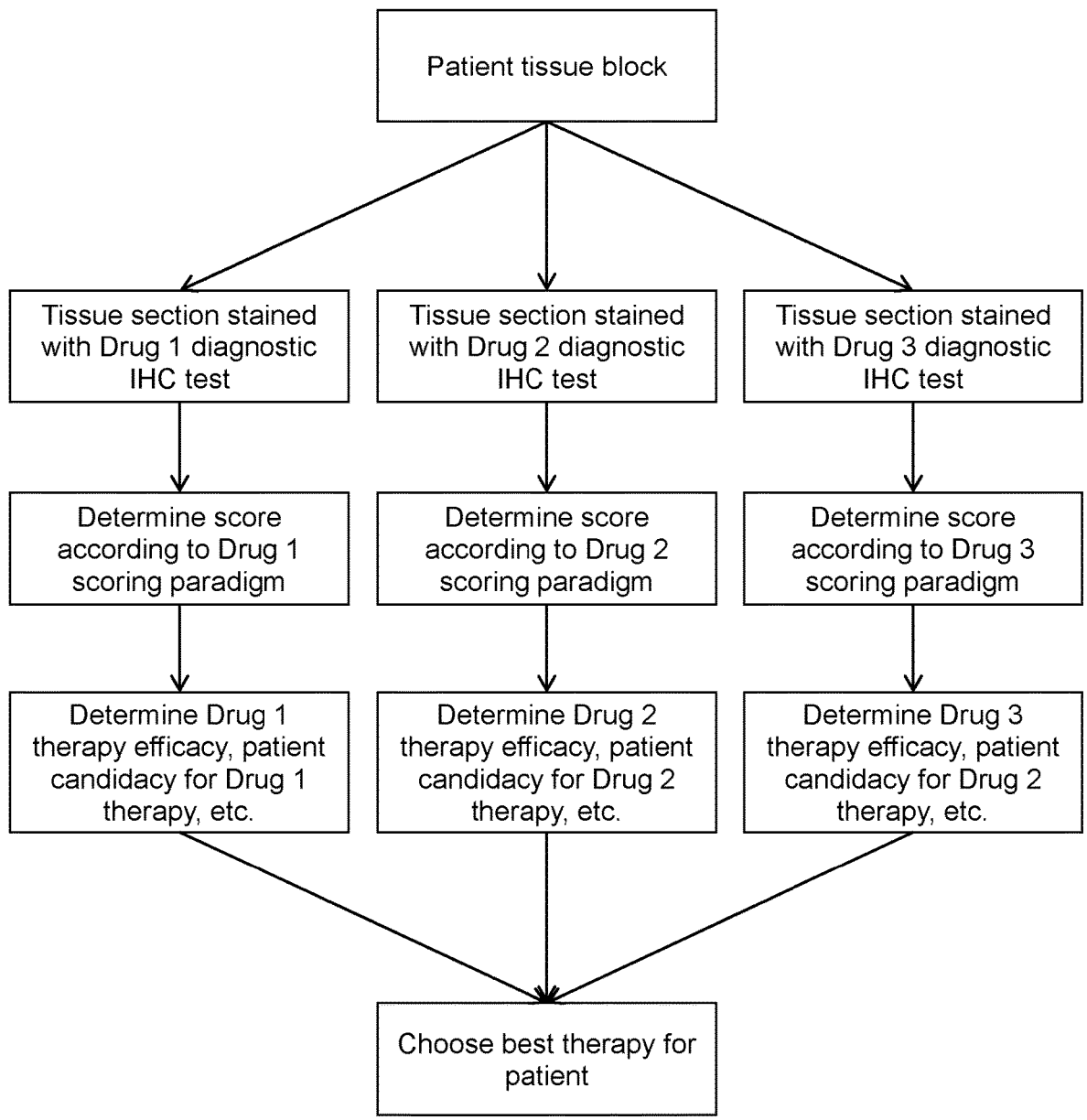
FIG. 1 illustrates the general method for determining the best method of treatment for a patient as exists in the prior art.
Figure 3:
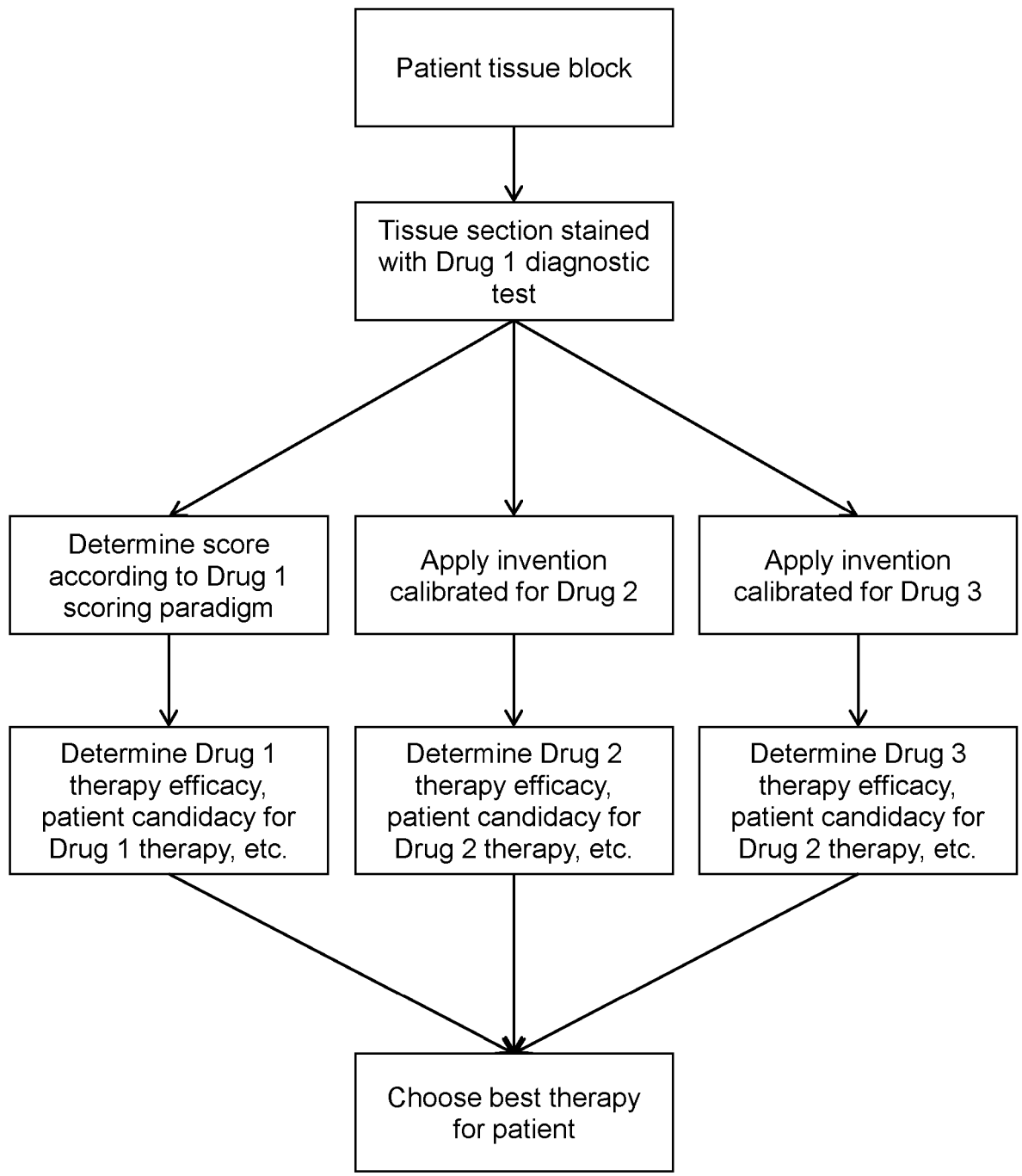
FIG. 3 illustrates a practical application of the present invention as a counterpoint for the method that exists in the prior art.

This paradigm can be used with a plurality of different CDx tests to determine which therapy, from the plethora of different drug and test paradigms available for a given illness, is the best for the patient. FIG. 3 shows the process by which this invention could be used for three different CDx tests for three different drugs based on a single tissue section. In comparison, in the prior art, three tissue sections would be needed for three separate CDx tests, as shown in FIG. 1.

In some embodiments, the test for Drug 1 is used in such a way that the concentration of a biomarker can be tied to a specific coordinate position within the tissue section. Multiple assay modalities are available that will link concentration of a biomarker to coordinate position within the tissue section, such as immunohistochemistry, immunofluorescent, chromogenic in situ hybridization, fluorescent in situ hybridization, and mass spectrometry imaging approaches. Other approaches are contemplated.

In a further embodiment, the image analysis features include morphometric features, localization features, neighborhood features, and staining features of the tissue objects within the tissue sample. Morphometric features are features related to the size, shape, area, texture, organization, and organizational relationship of tissue objects observed in a digital image. For example, and not limitation, morphometric features could be the area of a cell nucleus, the completeness of biomarker staining in a cell membrane, the diameter of a cell nucleus, the roundness of a blood vessel, lacunarity of biomarker staining in a nucleus, etc.

Localization features are features related to position of a feature in the tissue section, spatial relationships of tissue objects relative to each other, relationship of image analysis features between tissue objects in the tissue section, and distribution of image analysis features within a tissue object. Location can be determined based on an absolute (e.g., x and y location based on pixel dimensions of image, μm from center of image defined by pixel dimensions of image) or relative (e.g., x and y position of cells relative to a tissue feature of interest such as a vessel, polar coordinates referenced to the center of mass of a tumor nest) coordinate system (e.g., x-y-z coordinates, polar coordinates). Location for specific image objects can be defined as the centroid of the object or any position enclosed by the object extending from the centroid to the exterior limits of the object.

Neighborhood features are features related to tissue object morphology within a distance of an anchor tissue object, tissue object staining within a distance of an anchor tissue object, and morphology and/or staining between tissue objects within a distance of an anchor tissue object. For example, and not limitation, neighborhood features could be the average size or area of cells within 100 microns of an anchor cell or the quality or quantity of staining of cell nuclei within 500 microns of an anchor cell nucleus.

Staining features are features related to stain appearance, stain intensity, stain completeness, stain shape, stain texture, stain area, and stain distribution of specified IHC, ISH, and IF stains or dyes or amount of a molecule determined by MSI-based methodologies. Staining features are evaluated relative to tissue objects (e.g., average staining intensity in each cell in an image, staining level in a cell membrane, biomolecule expression in a nucleus).

Figure 4:
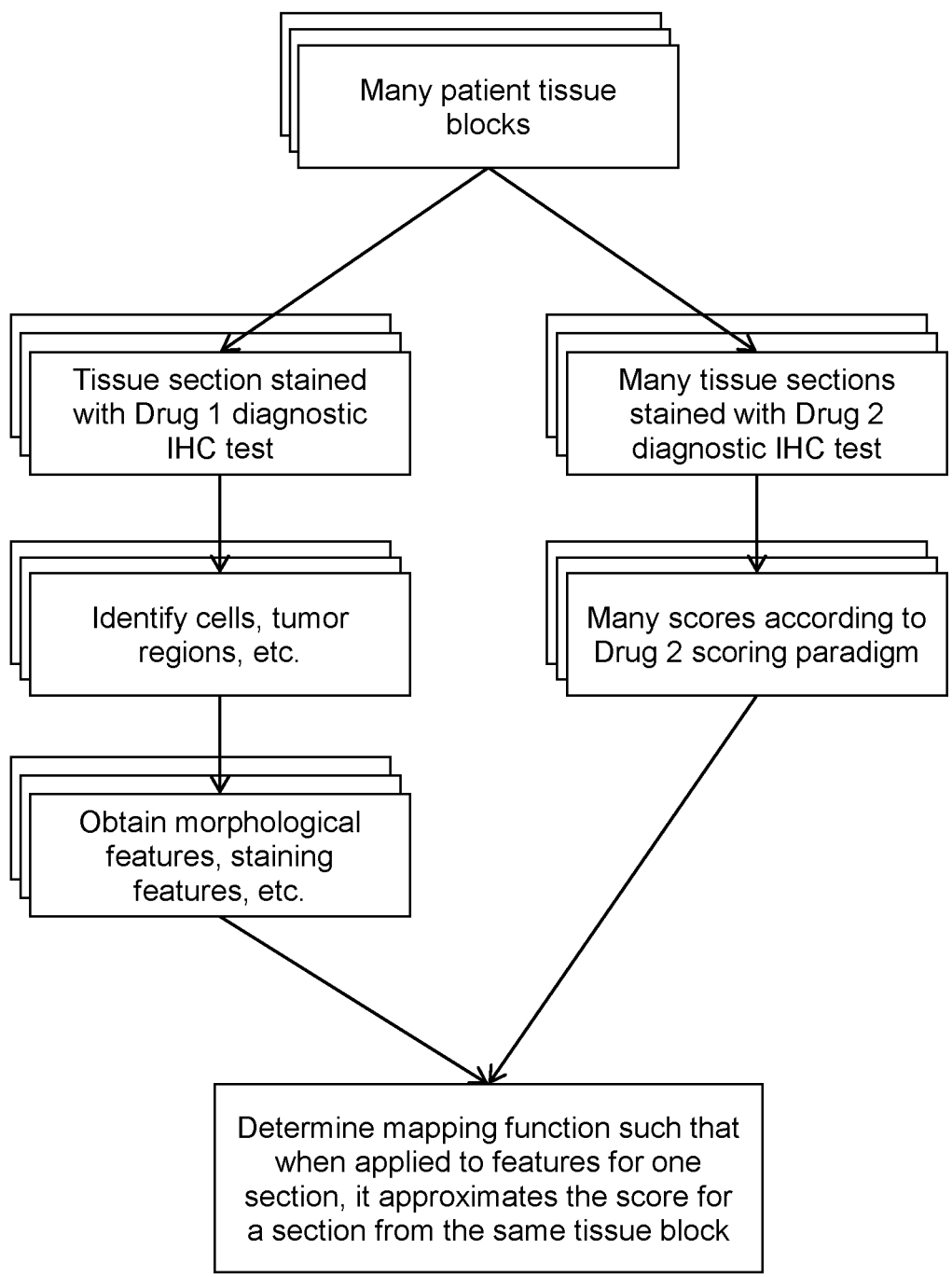
FIG. 4 illustrates how the method may be trained using machine learning.

In another embodiment, the mapping function may be a machine learning classifier, as seen in FIG. 4. This classifier may be trained using image analysis features from tissue sections that have been assayed with the test from Drug 1 and tissue sections stained with a plurality of other drug's CDx tests. The tissue sections for training the classifier may be such that they come from a plurality of tissue blocks, yet each tissue block provides tissue sections for use with each of Drug 1's CDx test and each of the other drug's CDx tests. It is also contemplated that each tissue block may provide only a portion of the total number of tests for training the classifier.

Typically, a single test is associated with a single therapeutic methodology. As such, Drug 1's test is associated with Drug 1 and Drug 2's test is associated with Drug 2. The present invention breaks this model by allowing Drug 2 to be evaluated after using Drug 1's test. In some embodiments, Drug 1 and Drug 2 target the same gene product or biologic pathway.

What is claimed is:

1. A method comprising:
   obtaining at least one digital image of a patient's tissue section which has been assayed with a first tissue-based test that obtains a diagnostic score for the first tissue-based test;
   applying an algorithm process, implemented by a computer, to the at least one digital image to extract at least one image analysis feature from at least one tissue object from the at least one patient's tissue section;
   applying a mapping function to the at least one image analysis feature to calculate a virtual diagnostic score which would have been obtained if the at least one patient's tissue section had been assayed by at least one second tissue-based test, wherein the virtual diagnostic score is independently calculated for each second tissue-based test; and
   determining a patient status for the patient based on the virtual diagnostic score, wherein the patient status is selected from the group consisting of diagnosis, disease severity, disease progression, candidacy for a therapy, and therapy efficacy.

2. The method of claim 1, further comprising comparing the diagnostic score for the first tissue-based test and the virtual diagnostic score for each second tissue-based test to select the most appropriate therapeutic methodology for the patient.

3. The method of claim 1, wherein the first tissue-based test evaluates the at least one patient's tissue section in a manner which can associate at least one biomarker and its concentration to a specific coordinate position in the tissue by at least one assay modality.

4. The method of claim 3, wherein the at least one assay modality is selected from the group consisting of immunohistochemistry, immunofluorescent, chromogenic in situ hybridization, fluorescent in situ hybridization, and mass spectrometry imaging approaches.

5. The method of claim 1, wherein the at least one image analysis feature is selected from the group consisting of morphometric features, staining features, localization features, and neighborhood features.

6. The method of claim 5, wherein the morphometric features are selected from the group consisting of size, shape, area, texture, organization, and organizational relationship.

7. The method of claim 5, wherein the staining features are selected from the group consisting of stain appearance, stain intensity, stain completeness, stain shape, stain texture, stain area, and stain distribution.

8. The method of claim 5, wherein the localization features are selected from the group consisting of position of a feature in the tissue section, spatial relationships of tissue objects relative to each other, relationship of image analysis features between tissue objects in the tissue section, and distribution of image analysis features within a tissue object.

9. The method of claim 5, wherein the neighborhood features are features related to tissue object morphology within a distance of an anchor tissue object, and tissue object staining within a distance of an anchor tissue object, and morphology and/or staining between tissue objects within a distance of an anchor tissue object.

10. The method of claim 1, wherein the mapping function is a machine learning classifier trained using image analysis features obtained from tissue sections that have been assayed with the first and each of the second tissue-based tests.

11. The method of claim 10, wherein the tissue sections that have been assayed with the first and each of the second tissue-based tests are groups of tissue sections taken from individual tissue blocks such that each tissue block provides tissue sections assayed with the first and a plurality of the second tissue-based test.

12. The method of claim 1, wherein the first tissue-based test is associated with a first therapeutic methodology and the second tissue-based test is associated with a second therapeutic methodology.

13. The method of claim 12, wherein the first and second therapeutic methodologies involve the same gene product or biologic pathway.

* * * * *